United States Patent
Ostrow

[19]

[11] Patent Number: 6,009,346
[45] Date of Patent: Dec. 28, 1999

[54] AUTOMATED TRANSDERMAL DRUG DELIVERY SYSTEM

[75] Inventor: Alvin S. Ostrow, Ra'anana, Israel

[73] Assignee: Electromagnetic Bracing Systems, Inc., Fort Lee, N.J.

[21] Appl. No.: 09/002,426

[22] Filed: Jan. 2, 1998

[51] Int. Cl.$^6$ ...................................................... A61N 1/30
[52] U.S. Cl. ................................ 604/20; 604/22; 604/95; 424/449
[58] Field of Search ................................ 604/20–22, 95; 424/449

[56] References Cited

U.S. PATENT DOCUMENTS 5,571,083  11/1996  Lemelson .
5,748,767   5/1998  Raab .

Primary Examiner—Mark Bockelman
Attorney, Agent, or Firm—William Nitkin

[57] ABSTRACT

An automated transdermal robotic treatment and drug delivery system to provide multimodal therapies and treatments to a patient. The movement of a robotic arm is preprogrammed to apply such treatment and medicine delivery to the skin of the patient in a desired sequence of movement. The robotic arm can fuirther be used for diagnosis and other medical treatments.

14 Claims, 3 Drawing Sheets

AUTOMATED TRANSDERMAL DRUG DELIVERY SYSTEM

BACKGROUND OF THE INVENTION

1. Field of the Invention

The present invention relates generally to a drug delivery system, and more particularly to a labor-saving device and method for the automated delivery of medication to a patient by means of various therapies such as ultrasound therapy, sonophoresis, phonophoresis or other therapies or any combination thereof.

2. Description of the Prior Art

Transdermal drug delivery systems are well known in the prior art. There are two methods by which drugs can be delivered through the skin: passive diffusion and active diffusion. Passive diffusion involves placing a concentration of a drug in a reservoir over the surface of the skin and allowing the drug to diffuse through the skin and into the muscles, tendons, joints and bloodstream. Due to natural skin barriers, few pharmaceuticals have been successfully passively diffused into the body. With passive diffusion, if a medicine is to be effective, it must work well at relatively low dosages and be of sufficiently small molecular size that the skin will allow it to enter the body. Drugs satisfying these criteria can be applied by a therapist massaging on an ointment containing the drug with his fingertips. Examples of patented patch devices are U.S. Pat. No. 5,533,995 to Corish et al; U.S. Pat. No. 5,358,483 to Sibalis; and U.S. Pat. No. 5,356,632 to Gross et al.

A more viable way for drugs to penetrate the skin's barriers is by means of an active energy source that pushes drug molecules through the skin and, at the same time, controls the rate of delivery. An energy-driven system will allow a greater quantity of medicine and medicine of a greater molecular size to be delivered in a shorter time frame. There are two general types of active transdermal drug delivery, iontopboresis and methods using ultrasonic waves as the driving source.

Ultrasonic methods include phonophoresis and sonophoresis. Phonophoresis refers generally to the use of sound waves to enhance the delivery of topically applied drugs. Sonophoresis is similarly defined as ultrasonically induced drug delivery by using high energy ultrasonic waves to drive drug molecules through the skin. A method for applying low frequency ultrasonic waves to cause cavitation of the skin to facilitate penetration by a medicine or cosmetic is described in U.S. Pat. No. 5,618,275 to Bock. U.S. Pat. No. 5,636,632 to Bommannan et al discloses a method for enhancing the skin's permeability to a drug. In this method, the drug is delivered while applying ultrasonic waves having a frequency above 10 MHz. Other prior art transdermal drug delivery systems include U.S. Pat. No. 5,421,816 to Lipkovker and U.S. Pat. No. 5,387,189 to Gory et al.

SUMMARY OF THE INVENTION

The present invention relates generally to a drug delivery system and provides a method to deliver treatment by means of a programmable robotic arm as a labor-saving device for delivering medication to a patient by means of attaching to the robotic arm devices to provide ultrasound therapy, I.e. sonophoresis, phonophoresis, electromagnetophoresis, iontophoresis or any combination thereof for physiotherapy and drug delivery energized by traditional electrical, magnetic and/or ultrasound wave drivers. The robotic arm can also alternately be used for physiotherapy, diagnostic or surgical purposes.

The device consists of a titration system to dispense and deliver a permanent drug, cream or gel coupling medium to the head of an ultrasound device compatible with commonly used dual ultrasound and electrotherapy console devices already available on the market. The selected device is held by an automated arm programmed by an operator. In one embodiment a sound head is attached to the robotic arm, whereby the device correctly positions the sound head for applying treatment and is energized from a console to deliver modes of ultrasound therapy, electrotherapy, sonophoresis, iontophoresis, or all combined simultaneously.

The device can provide electromagnetophoresis and phono-electromagnetophoresis as well as electroinfusion therapies.

One object of the invention is the optimization of skin penetration enhancement by such electroinfusion to facilitate ionizable drug delivery across the skin through a membrane electrode driven by multiple applied electrical potential. More specifically electroinfusion uses various types of electrical potentials and multiple drivers with varying electrical potentials and frequencies to enhance transdermal drug delivery.

A further goal of this invention is to use the robotic arm for medical applications beyond physical therapy to include manipulation of diagnostic instruments, such as diagnostic ultrasound for obstetrics, cardiology, for example.

The transdermal drug delivery device of this invention includes a robotic arm, the movement of which is programmed to apply treatment to a patient's skin and surface tissues through an ultrasonic applicator which delivers a drug medium by using ultrasonic waves as a driver to penetrate the skin membrane. The device includes one or more ultrasonic applicators adapted to deliver a permanent drug, cream or gel simultaneously with sonophoretic treatment. Such treatment can include one or more ultrasonic therapy, sonophoresis or phonophoresis. A sound head on the ultrasonic applicator is attached to the robotic arm, which arm correctly positions the sound head for applying treatment. Sound heads can also be used for diagnosis by displaying the results on a monitor such as in fetal sonograms. A physician can remotely control the sound head to position if by giving directions to the robotic arm. The robotic arm is attached to a central support which includes a rack for holding one or more drug reservoirs and a programmable controller with a keyboard console. The entire device can be contained on a portable trolley on wheels, allowing it to be easily moved between patients and positioned in a desired location.

It is a further object of this invention to provide a robotically controlled transdermal drug delivery device which can be programmed to apply a drug by ultrasonic wave therapy in a prescribed sequence to the skin of a patient and to apply traditional electrical physiotherapy in absence of the therapist. Other therapies and diagnostic procedures can be performed by the robotic arm of this invention including, but not limited to, photophoresis. Laser treatments for surgery, various therapies and for diagnostic procedures can be accomplished as well as transdermal drug delivery enhanced by laser beams directed on such medication on the body by the robotic arm.

It is a yet further object of this invention to provide a portable system that can be easily positioned close to a patient and moved between patients.

DESCRIPTION OF THE PREFERRED EMBODIMENT(S)

Figure 1:
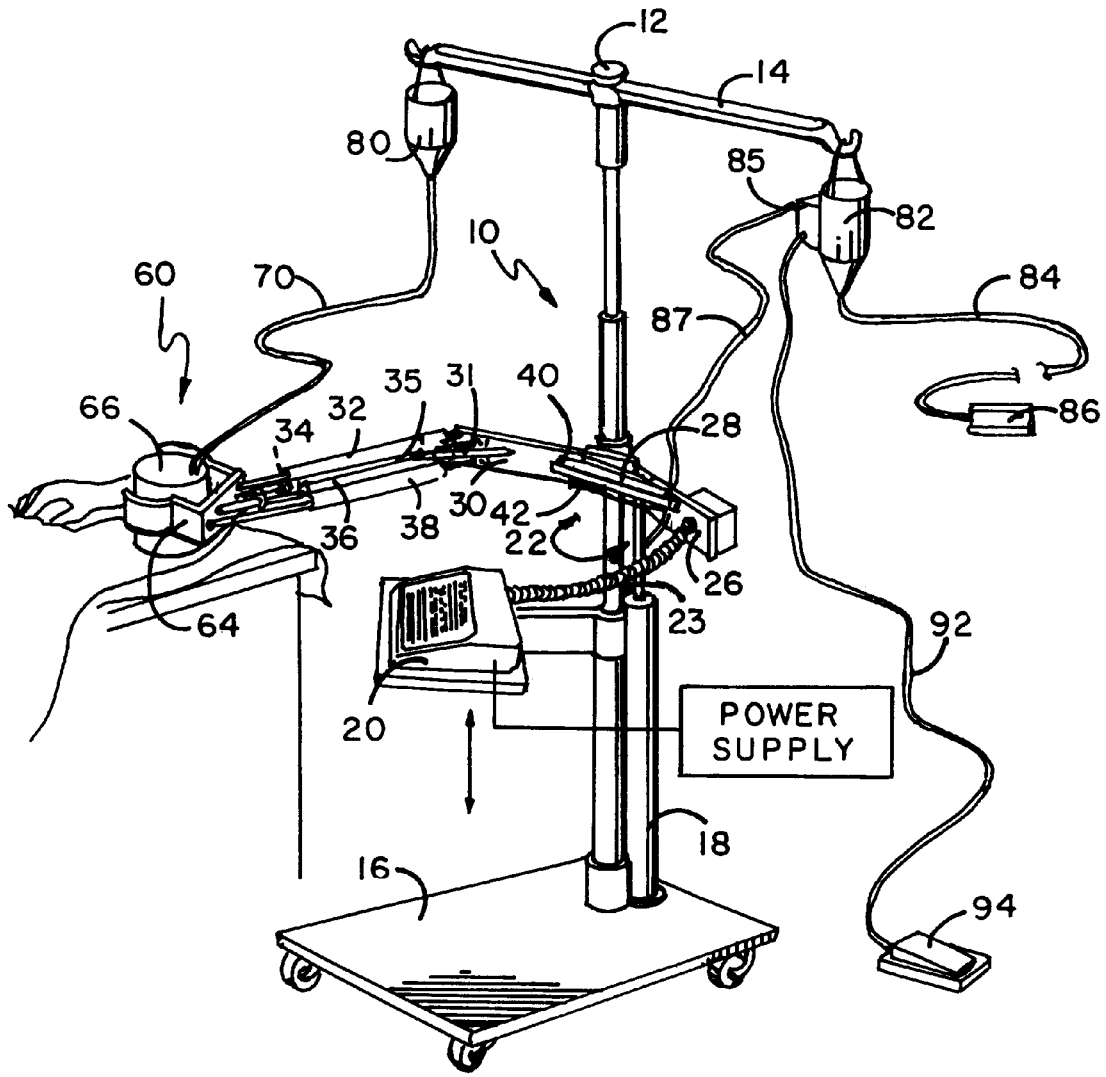
FIG. 1 illustrates a perspective view of the transdermal drug delivery device of this invention showing the device applying treatment to a patient's arm.

FIG. 1 illustrates the tansdermal drug delivery device of this invention arranged to apply treatment to a patient's arm. Seen in this view is robotic arm 10 which includes upper arm 30 with a fixed counterbalance 26 acting as a stay to support arm 30 along with forearm members 32, 34, 36, and 38, and ultrasound applicator 60. Hydraulic pistons 40 and 42 move arm 30 and forearm 35 as directed by programmable controller 20 which includes a computer. Robotic arm 10 is attached to central support 12 and hydraulic ram 18. Arm 10 can be moved up and down to a desired height by hydraulic ram 18. Lateral movement of arm 10 is facilitated by upper arm joint 28, which movement is controlled by programmable controller 20. Programmable controller 20 is attached to central support 12 at a point below robotic arm 10, but programmable controller 20 could be positioned above the robotic arm attachment in an alternate embodiment. The operation and setting of robotic arm 10 can be supervised by a physiotherapist or clinician who can optionally program programmable controller 20 for robotic operation or manual operation. Programmable controller 20 includes programs to provide a guidance system for robotic arm 10 to operate for a desired time, number of repetition, direction of movement, and positioning of the treatment head attachment. Wires from programmable controller 20 deliver electronically coded messages to the various components of robotic arm 10 by means of an extendible wire head 22. Robotic arm 10 is supported on a movable trolley 16 attached to central support 12 as well as being supported on hydraulic ram 18. Trolley 16 has a wheel-locking mechanism on its wheels to prevent unwanted movement. Robotic arm 10 and upper arm 30 are attached to central support 12 through upper arm joint 28 which has at one end support counterbalance 26. Support counterbalance 26 generally provides balance and support for arm 10.

Figure 2:
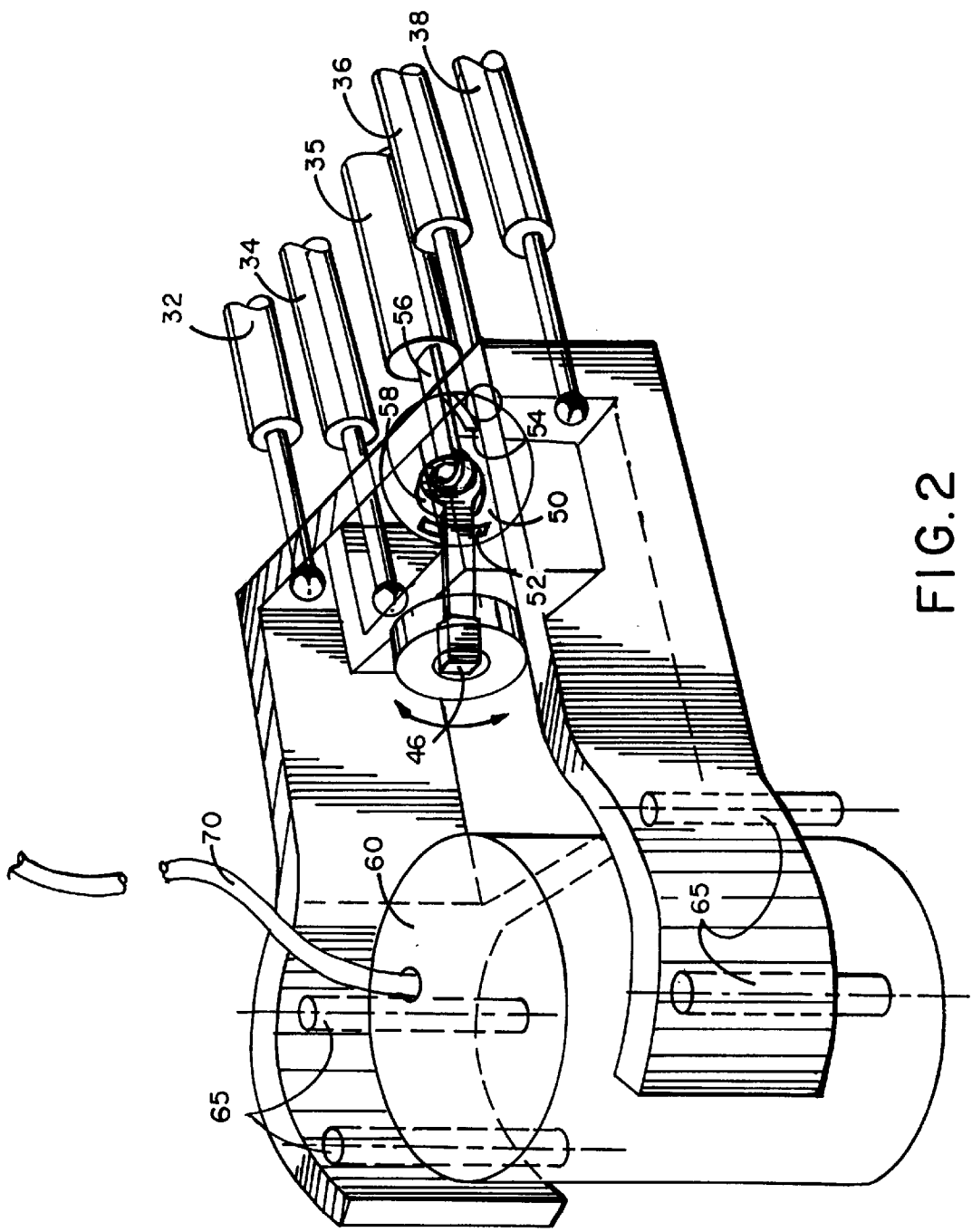
FIG. 2 illustrates a perspective view of the area around the pivot member, showing an internal view of the hooking engagement of the pivot member.

Upper arm 30 extends horizontally in the direction opposite support counterbalance 26 and is connected to forearm central shaft 35 as well as pivotally connected to four forearm members 32, 34, 36 and 38. Forearm members 32, 34, 36 and 38 can be extendible and retractable pistons to move hand clamp 66 holding ultrasound applicator 60 up and down and left and right which movements are controlled by programmable computer 20. Pivot member 44 includes internal hook 56 which passes through hook aperture 54 and engages in coupling 58 inside of pivot member 44. Hook 56 and coupling 58 slideably move through vertical aperture 52 and horizontal aperture 54. The movement of ultrasound applicator 60 to provide treatment to particular locations is facilitated by movement of hand clamp 66, as seen in FIG. 2.

Drip feed tube 70, as seen in FIG. 1, and feed tube 84 deliver medication, gels, or lotions such as from reservoirs 80 and 82 supported on horizontal support rack 14. Reservoir 82 can dispense, for example, a gel pumped by pump 85 controlled through electric line 87 down tube 84 to ultrasonic head 86 which is to be positioned on the patient.

Ultrasound waves can also be transmitted through applicator tube 64 in sound head 60 along with regulated doses of medication from the one or more drip feed tubes. Ultrasound waves are applied by sound head 66 and regulated by instructions which a clinician inputs into programmable controller 20.

The device of this invention provides an interchangeable head 86 for non-drug application of gel that can be operated automatically by a foot pedal 94 to control pump 85 connected by wire 92 to feed tube 84 which can be connected to dispensing head 86 to dispense gel onto the patient, all controlled by robotic arm 30.

Figure 3:
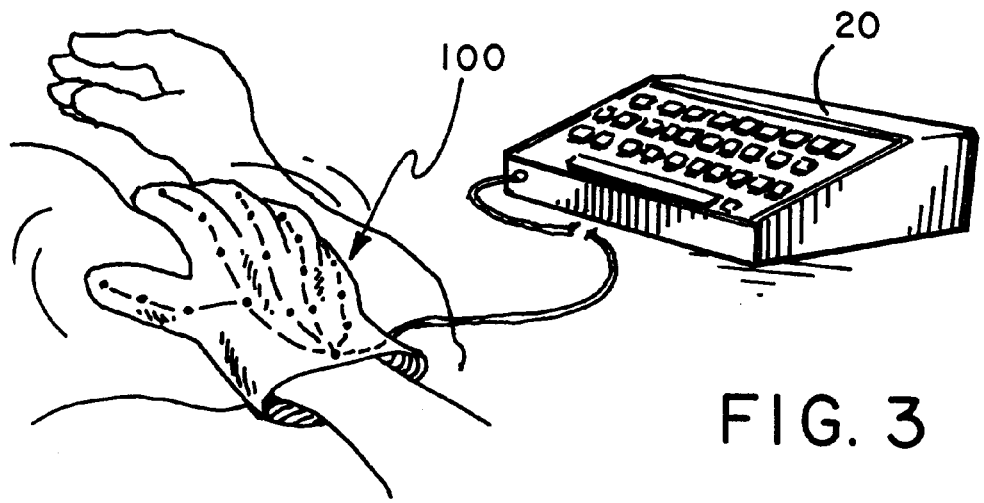
FIG. 3 illustrates a perspective view of a remote control glove to direct a computer on placement of the robotic arm.
Figure 4:
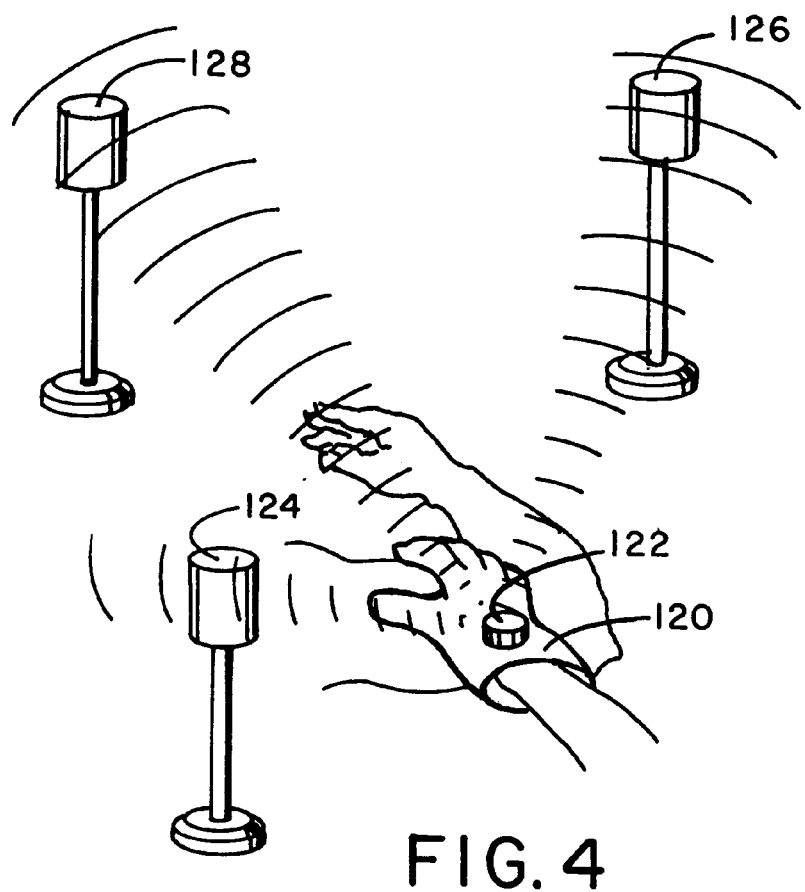
FIG. 4 illustrates a perspective view of an alternate embodiment of a remote control glove to direct a computer on placement of the robotic arm.

FIG. 3 illustrates the use of a virtual reality glove 100 interconnected to programmable controller 20. The glove can sense the movements of the therapist's hand on the patient while programmable controller 20 makes a record of such movement. Such a glove 120, seen in FIG. 4, can have its position detected by triangulation sensors 124, 126 and 128 which sense the position of detector head 122 on glove 120 and direct such information to the programmable controller computer. Programmable controller 20 then directs robotic arm to duplicate repetitively such movement to direct the treatment head over the patient, thereby saving the continued effort of the therapist and eliminating the need for the therapist to be present. This technology frees up the therapist for other work and allows the therapist to treat many patients at the same time. Current three-dimensional computer technology further allows the treatment head itself to be utilized to produce a three-dimensional "map" of the treatment area. Many types of known sensors 65 able to detect proximity, as seen in FIG. 2, can be used within the treatment head to help determine its position and to transmit such position information to the computer. The computer later, by using such information, can direct the treatment head to the appropriate position on the patient, even calculating the patient's body positioning from known data to expand treatment automatically once the treatment head's position is determined on the patient. Four sensors can be utilized to help maintain the perpendicularity of the treatment head to the patient's skin surface. The treatment head can also be fitted with pressure sensors to maintain a comfortable, constant pressure on the skin's surface.

The device of this invention can be utilized to provide a variety of treatments, including introducing drugs transdermally by applying phonophoresis through one or more ultrasound applicators, and/or applying singular or combination modes of ultrasound therapy. The device provides an automatic, monitored, uniform, and consistent supply of medication through one or more drip feed tubes while one or more sound heads are programmed to simultaneously apply the aforementioned forms of treatment.

Although the present invention has been described with reference to particular embodiments, it will be apparent to those skilled in the art that variations and modifications can be substituted therefor without departing from the principles and spirit of the invention.

I claim:

1. A device for delivering a medication transdermally to the skin of a patient, comprising:
    a central support;
    a programmable controller with a computer associated with said central support, said computer being programmable and adapted to transmit instructions for applying transdermal treatment of a medication to an area of a patient's body;
    a robotic arm having a first end and a second end, said first end mounted on said central support, said robotic arm capable of receiving said instructions from said computer and moving to desired positions according to said instructions for duplicating the motion of repetitive hand movements formerly manually done by a clinician;

medication delivery means including a reservoir;

a medication feed tube having a first end and a second end, said first end of said medication feed tube attached to said reservoir; and a treatment head having a first end and a second end, said first end attached to said second end of said robotic arm, said treatment head including means for receiving said second end of said medication feed tube containing said medication for applying said medication to the skin of said patient with said repetitive movements.

2. A device for delivering a medication transdermally to the skin of a patient by a clinician, comprising:

a central support having a top;

a programmable controller with a computer associated with said central support, said computer being programmable and adapted to transmit instructions for applying transdermal treatment of a medication to a patient;

a robotic arm having a first end and a second end, said first end mounted on said central support, said robotic arm capable of receiving said instructions from said computer and moving to desired positions according to said instructions for duplicating the motion of repetitive hand movements formerly manually done by said clinician;

medication delivery means;

a medication feed tube having a first end and a second end, said first end connected to said medication delivery means;

a treatment head having a first end and a second end, said first end attached to said second end of said robotic arm, said treatment head including means for receiving said second end of said medication feed tube containing said medication for applying said medication to the skin of said patient;

wherein said central support, said robotic arm, and said treatment head are contained on a portable trolley allowing for ease of positioning on a patient and for ease of movement of said device; and further including a support rack mounted on the top of said central support, said support rack supporting one or more medication delivery means each comprising a reservoir holding a medication.

3. The device of claim 2 wherein said treatment head has means for delivering a treatment selected from the group of sonophoresis, phonophoresis, photophoresis, iontophoresis and magnetophoresis.

4. The device of claim 2 wherein said treatment head has means for providing ultrasound and electrotherapy in conjunction with said delivery of medication to said patient through said treatment head.

5. The device of claim 2 further including a first reservoir holding a drug and second reservoir holding a drug-free gel, said first and second reservoir each having a feed tube attached thereto.

6. The device of claim 5 further including:

means for receiving said feed tube from said second reservoir and dispensing said gel from said treatment head onto the skin of said patient.

7. The device of claim 6 further including a foot pedal pump allowing for clinician-actuated operation of said device to dispense said gel.

8. The device of claim 2 wherein said drug is a fluid.

9. The device of claim 2 wherein said drug is a gel.

10. The device of claim 9 wherein said gel is a drug-free medium.

11. The device of claim 10 further including a foot pedal pump allowing for clinician-actuated operation of said device to dispense said gel.

12. The device of claim 2 further including a pivot joint which includes a hook and coupling engagement disposed at said second end of said robotic arm between said robotic arm and said head to facilitate movement of said ultrasonic applicator.

13. The device of claim 12 further including the use of a glove with sensors to determine a patient's position and means to store said information of said position in said computer to direct the movement of said ultrasonic applicator.

14. The device of claim 2 wherein said drug is a lotion.

* * * * *